(12) United States Patent
Gordon

(10) Patent No.: US 6,434,762 B2
(45) Date of Patent: Aug. 20, 2002

(54) STOOL COLLECTING APPARATUS

(76) Inventor: Steven N. Gordon, 305 E. 86th St., Apt. 14MW, New York, NY (US) 10028

( * ) Notice: Subject to any disclaimer, the term of this patent is extended or adjusted under 35 U.S.C. 154(b) by 0 days.

(21) Appl. No.: 09/755,083

(22) Filed: Jan. 8, 2001

Related U.S. Application Data

(60) Provisional application No. 60/175,306, filed on Jan. 10, 2000.

(51) Int. Cl.[7] .............................................. A47K 11/04
(52) U.S. Cl. ............................... 4/483; 4/315; 604/326; 604/322
(58) Field of Search ........................... 4/483, 485, 479, 4/450, 451, 452, 453, 661, 315, 144.2, 144.3, 144.4; 604/322, 326; 422/55–58; 436/66; D23/309, 311; D24/123, 122

(56) References Cited

U.S. PATENT DOCUMENTS

| | | | |
|---|---|---|---|
| 2,537,504 A | * 1/1951 | Anderson | 4/239 |
| 2,603,795 A | 7/1952 | Terlizzi | |
| 2,840,826 A | * 7/1958 | Ebbesen et al. | 4/661 |
| 3,061,840 A | 11/1962 | Presseisen | |
| 3,095,578 A | * 7/1963 | Stanford | 4/144.2 |
| 3,346,883 A | * 10/1967 | Ersek | 4/661 |
| 3,540,433 A | 11/1970 | Brockman | |
| 3,588,921 A | * 6/1971 | Nagel | 4/245.4 |
| 3,711,871 A | * 1/1973 | Sherin | 4/144.1 |
| 3,754,287 A | * 8/1973 | Taylor | 4/661 |
| 3,775,777 A | * 12/1973 | Roberts, Jr. | 4/661 |
| 4,011,606 A | * 3/1977 | Scarfield et al. | 4/457 |
| 4,309,782 A | * 1/1982 | Paulin | 4/661 |
| 4,445,235 A | 5/1984 | Slover et al. | |
| 4,720,880 A | 1/1988 | Barreau | |
| 4,935,969 A | 6/1990 | Farnsworth | |
| 4,996,727 A | 3/1991 | Wyatt | |
| 5,316,386 A | * 5/1994 | Moore | 383/10 |
| 5,337,426 A | 8/1994 | Matusewicz et al. | |
| 5,412,819 A | 5/1995 | Matusewicz et al. | |
| 5,463,782 A | * 11/1995 | Carlson et al. | 4/661 |
| 6,070,277 A | 6/2000 | Thomas | |
| 6,112,339 A | * 9/2000 | Nichols et al. | 4/484 |
| 6,116,780 A | * 12/2000 | Young et al. | 383/44 |
| 6,212,698 B1 | * 4/2001 | Stingley et al. | 4/315 |

* cited by examiner

Primary Examiner—Charles R. Eloshway
Assistant Examiner—Huyen Le
(74) Attorney, Agent, or Firm—Nixon & Vanderhye P.C.

(57) ABSTRACT

A stool collecting apparatus is simple in construction and inexpensive to manufacture and provides an easy to use and contamination free apparatus for collecting a stool sample. The device includes a disposable strip spanning at least a width of a toilet seat having adhesive sections at ends thereof and an opening section between the ends. The opening section includes an opening through the disposable strip and a lip spanning a periphery of the opening. A sealable stool receptacle is removably secured to the lip adjacent the opening section. After a sample is deposited, the receptacle can be easily removed from the disposable strip and sealed for subsequent processing. The strip, with or without a seat cover, can then be discarded.

10 Claims, 3 Drawing Sheets

STOOL COLLECTING APPARATUS

This application claims the benefit of U.S. Provisional Patent Application Serial No. 60/175,306, filed Jan. 10, 2000, the entire content of which is herein incorporated by reference.

BACKGROUND OF THE INVENTION

The present invention relates generally to sanitary medical devices and, more particularly, to a convenient and sanitary stool collecting apparatus.

Traditionally, the diagnosis of a potential intestinal ailment begins with an analysis of the patient's stool. A stool sample is one of the most conventional, elementary and least expensive methods of determining which bacteria, or, less often, parasite, may be infecting a patient. When isolated from stool samples, live colon cells additionally provide health care professionals with an early warning system to detect colorectal cancer. In that colon cancer is responsible for approximately fourteen percent (14%) of all cancer related deaths in the United States, a non-invasive, readily available and easy to use screening examination would provide health care providers with ample time to detect abnormal growths or polyps (from three to five years before a malignancy appears) before they turn cancerous.

Attempts have been made to provide devices that provide a convenient means for enabling a patient to collect a stool sample for subsequent medical analysis. Typically, the more simply constructed devices are difficult to use in a sanitary manner, thus making it difficult to preserve the sample's homogeneity and purity, while more complicated devices are expensive to manufacture.

SUMMARY OF THE INVENTION

It is thus an objective of the present invention to provide a stool collecting apparatus that allows a patient to collect a stool sample (whether solid or liquid), without another's assistance, with no fear of touching the sample, at a doctor's office or in the privacy and comfort of home and to supply the doctor with the sample in a hermetically sealed package. The apparatus includes a disposable strip, with or without a seat cover, that supports a sealable stool receptacle in an appropriate position relative to a toilet seat. Once the sample is deposited in the receptacle, the receptacle can be easily removed from the disposable strip and sealed for later processing.

In accordance with an exemplary embodiment of the invention, a stool collecting apparatus attachable to a toilet seat includes a disposable strip spanning at least a width of the toilet seat, the disposable strip having adhesive sections at ends thereof and an opening section between the ends. The opening section includes an opening through the disposable strip and a lip spanning the periphery of the opening. A sealable stool receptacle is removably secured to the lip adjacent the opening section. A peel-away backing is preferably removably secured over each of the adhesive sections. The lip may be threaded on an outside thereof, wherein the sealable stool receptacle includes internal threads at a collar thereof that are sized corresponding to the threaded lip for engaging the threaded lip. In this context, the sealable stool receptacle may be perforated adjacent the collar for effecting removal of the collar.

In one embodiment, a disposable seat cover shaped corresponding to the toilet seat is coupled with the disposable strip. The disposable seat cover includes adhesive sections for securing the seat cover and attached disposable strip to the toilet seat. The peel-away backing may be removably secured over the adhesive sections of the disposable seat cover.

In preferred embodiments, the sealable stool receptacle is a plastic zip-lock bag, and the disposable strip is formed of paper.

In accordance with another exemplary embodiment of the invention, a stool collecting kit includes sealable receiving structure for receiving and sealing a stool sample, and structure for releasably supporting the sealable receiving structure in a convenient position, wherein the supporting structure is disposable.

BRIEF DESCRIPTION OF THE DRAWINGS

These and other aspects and advantages of the present invention will be described in detail with reference to the accompanying drawings, in which.

DETAILED DESCRIPTION OF PREFERRED EMBODIMENTS

Figure 1:
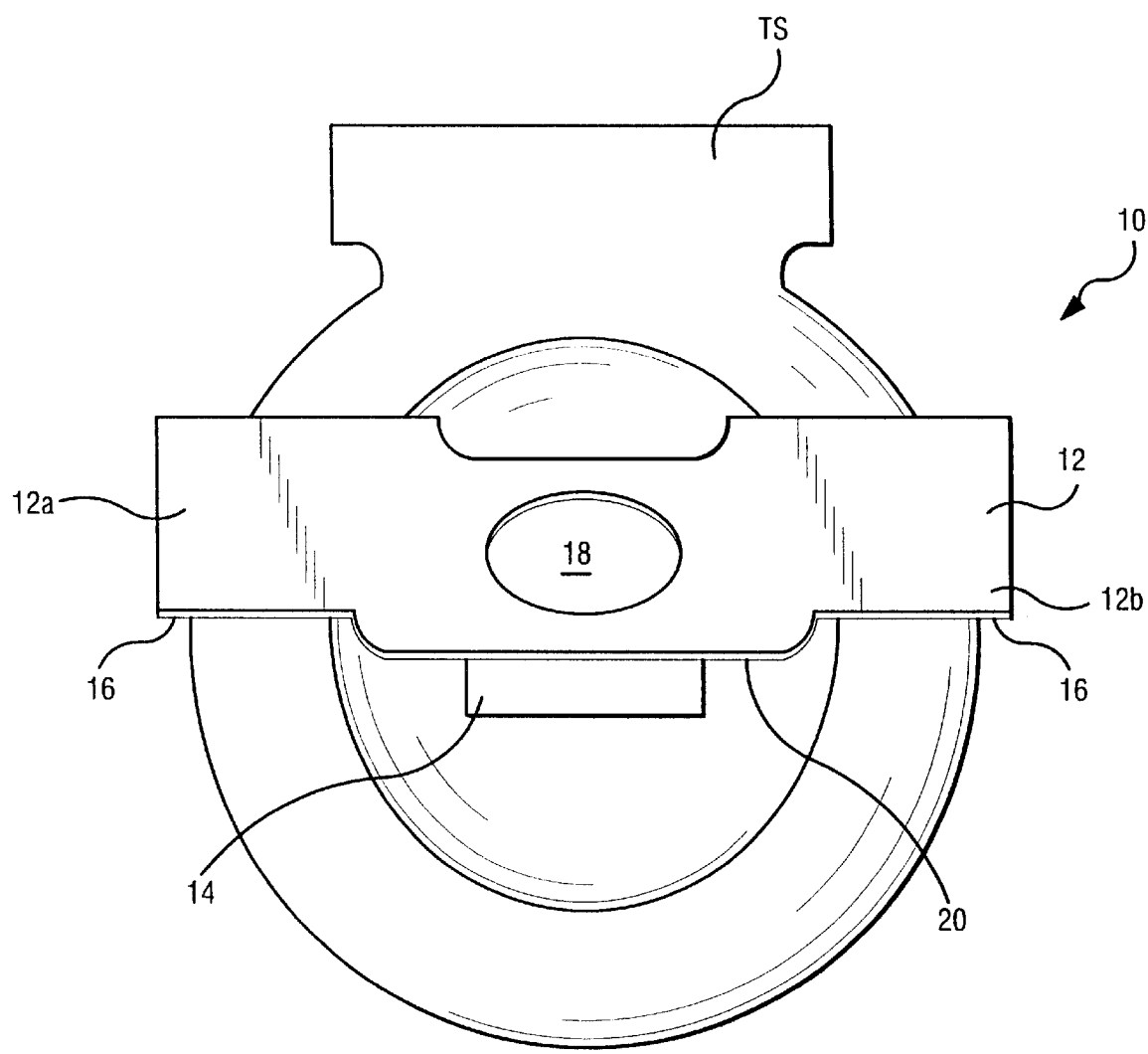
FIG. 1 illustrates the stool collecting apparatus of the invention secured to a toilet seat.

With reference to FIG. 1, the stool collecting apparatus 10 of the invention in a first embodiment is secured directly to a toilet seat TS. The apparatus 10 includes a disposable strip 12 preferably formed of paper or other suitably disposable material, and a stool receptacle 14 that is removably secured to the disposable strip 12. The strip 12 spans at least a width of a conventional toilet seat, and ends thereof 12a, 12b are provided with an adhesive on an underside to secure the strip 12 to the toilet seat TS. Preferably, the strip is long enough so that it does not become flush with the patient's buttocks when sitting on the toilet seat. A peel-away backing 16 may be secured to the strip 12 over the adhesive to facilitate storage of the apparatus 10 prior to use.

Figure 3:
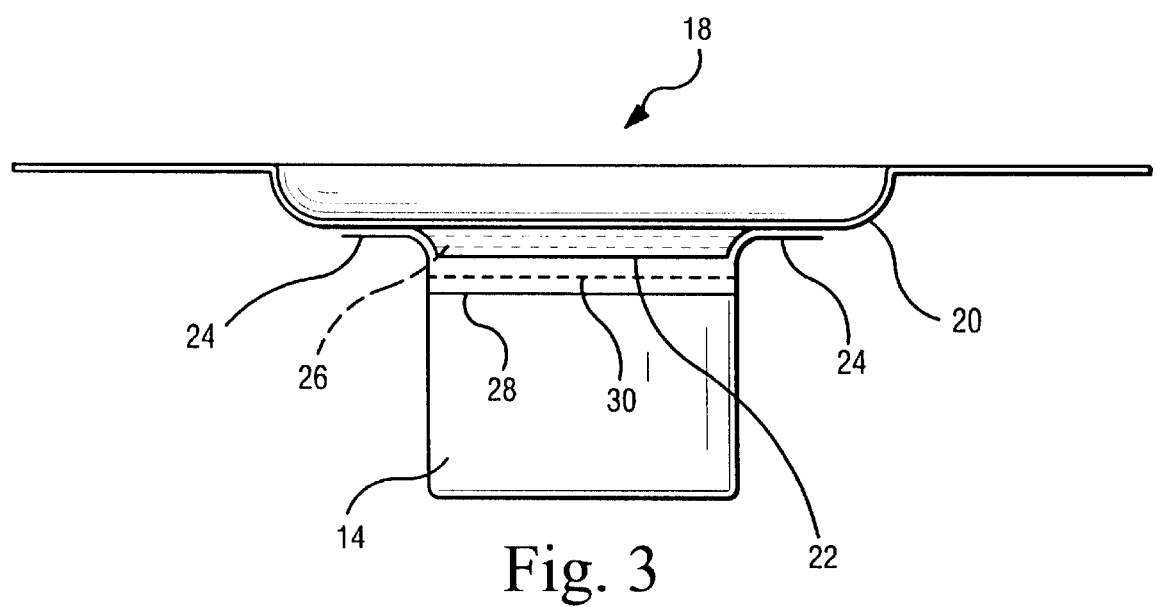
FIG. 3 is a side view of the stool collecting apparatus according to the present invention.

A center section of the strip 12 includes an opening 18 and a lip section 20 surrounding the opening as shown in FIGS. 1 and 3. The lip section 20 leads to a lip 22 defining a circumference of the opening 18.

With continued reference to FIG. 3, the stool receptacle 14 is removably secured to the lip section 20 via an adhesive. In one arrangement, the stool receptacle 14 includes attachment wings 24 that removably secure the stool receptacle 14 to the lip section 20. After a sample is deposited in the receptacle 14, the receptacle 14 can be separated from the strip 12 via the attachment wings 24. Alternatively, the main portion of the receptacle 14 may be secured to the attachment wings 24 with a perforation 30, and the perforation can be bursted for removing the receptacle 14 from the strip. In still another alternative, the lip 22 may include threads 26 so that the stool receptacle 14 with a threaded collar can be threaded onto the strip 12. This arrangement may also include a burstable perforation so the user is not required to rotate the stool receptacle 14 after depositing the sample.

The receptacle 14 is preferably a sealable latex or plastic bag such as a zip-lock bag. The seal 28 may be formed as part of the attachment wings 24 or in the event of perforated attachment wings, the seal may be disposed at an upper portion of the receptacle 14 as shown in FIG. 3. In still another arrangement, an additional perforation may be provided below the seal so that a collar of the stool receptacle 14 with the seal, threads or the like can be removed by the laboratory technician for processing. The lip section 20 of the strip 12 thus extends into the stool receptacle 14 to insure that the outside of the stool receptacle 14 does not become contaminated by the patient's stool and so that a patient, technician or doctor can handle the stool receptacle 14 without fear of touching the sample. Before use, the receptacle 14 is preferably folded flat to minimize storage space.

Figure 2:
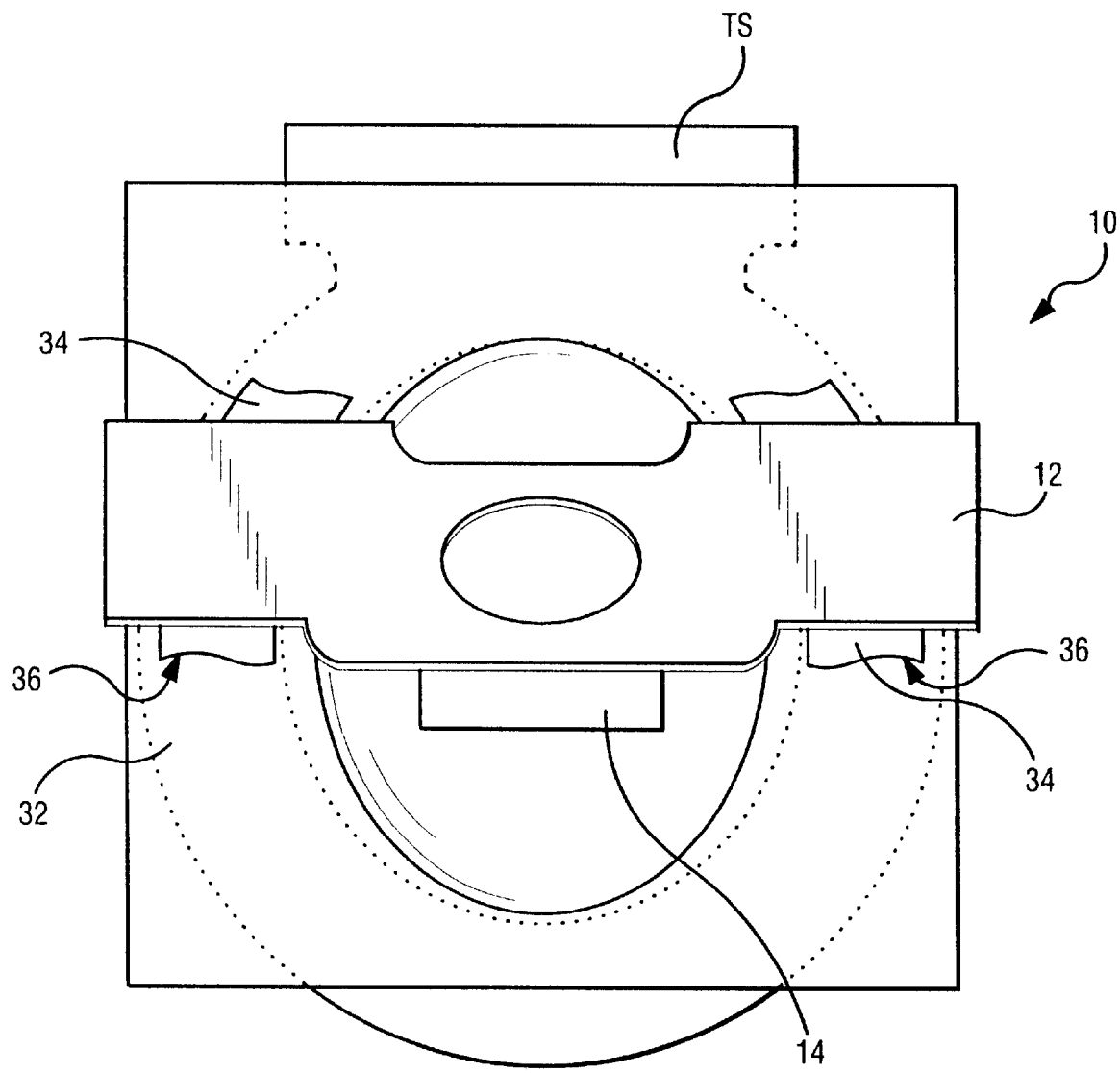
FIG. 2 illustrates the stool collecting apparatus of the invention including a protective toilet seat cover.

FIG. 2 illustrates an alternative embodiment of the invention that is particularly suited for use in a doctor's office or other non-home location. The apparatus 10 in FIG. 2 includes the same components of the apparatus described in the first embodiment, except that the strip 12 is secured to a disposable seat cover 32 as opposed to being secured directly to the toilet seat TS. The seat cover 32 includes adhesive sections 34 for securing the seat cover 32 and attached disposable strip 12 to the toilet seat TS. In this arrangement, the peel-away backings 36 are secured over the adhesive sections 34 of the seat cover 32. In this embodiment, the strip 12 is secured to the seat cover 32 in an appropriate position relative to the toilet seat and the user's body to facilitate collection of the stool sample.

In use, the user secures the strip 12 or strip 12 and cover 32 to the toilet seat TS after removing the peel-away backings 16 or 36. After depositing a sample in the stool receptacle 14, the strip 12 or cover 32 and strip 12 are lifted from the toilet seat TS, and the stool receptacle 14 is separated from the strip 12. The stool receptacle can then be sealed via the seal 28, and the strip 12 or strip 12 and cover 32 can be discarded.

The apparatus according to the invention is easy to use and inexpensive to manufacture. The patient can deposit a stool sample in the stool receptacle without fear of touching the sample, and the sealed receptacle is free from human and/or foreign contamination (whether from the patient's hands, urine leakage, toilet bowl water, possible pollutants from the otherwise used collection receptacle or during transportation in an otherwise non-hermetically sealed container), precluding the possibility of requiring a replacement sample.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A stool collecting apparatus attachable to a toilet seat, the stool collecting apparatus comprising:
    a disposable strip spanning at least a width of the toilet seat, the disposable strip having adhesive sections at ends thereof and an opening section between the ends, wherein the opening section includes an opening through the disposable strip and a lip spanning a periphery of the opening; and
    a sealable stool receptacle removably secured to the lip adjacent the opening section and supported only by the disposable strip during use, the sealable stool receptacle being independently sealable after removal from the lip of the disposable strip.

2. A stool collecting apparatus according to claim 1, further comprising a peel-away backing removably secured over each of the adhesive sections.

3. A stool collecting apparatus according to claim 1, wherein the lip is threaded on an outside thereof, and wherein the sealable stool receptacle comprises internal threads at a collar thereof, the internal threads being sized corresponding to the threaded lip for engaging the threaded lip.

4. A stool collecting apparatus according to claim 3, wherein the sealable stool receptacle is perforated adjacent the collar for effecting removal of the collar.

5. A stool collecting apparatus according to claim 1, further comprising a disposable seat cover shaped corresponding to the toilet seat, the disposable strip being attached to the disposable seat cover, wherein the disposable seat cover includes adhesive sections for securing the seat cover and attached disposable strip to the toilet seat.

6. A stool collecting apparatus according to claim 5, further comprising a peel-away backing removably secured over the adhesive sections of the disposable seat cover.

7. A stool collecting apparatus according to claim 1, wherein the sealable stool receptacle is a latex or plastic zip-lock bag.

8. A stool collecting apparatus according to claim 1, wherein the disposable strip is formed of paper.

9. A stool collecting apparatus attachable to a toilet seat, the stool collecting apparatus comprising:
    a disposable strip spanning at least a width of the toilet seat, the disposable strip having adhesive sections at ends thereof and an opening section between the ends, wherein the opening section includes an opening through the disposable strip and a lip spanning a periphery of the opening; and
    a sealable stool receptacle removably secured to the lip adjacent the opening section, wherein the sealable stool receptacle comprises a collar, and wherein the sealable stool receptacle is perforated adjacent the collar for effecting removal of the collar.

10. A stool collecting apparatus attachable to a toilet seat, the stool collecting apparatus comprising:
    a disposable strip spanning at least a width of the toilet seat, the disposable strip having adhesive sections at ends thereof and an opening section between the ends, wherein the opening section includes an opening through the disposable strip and a lip spanning a periphery of the opening; and
    a sealable stool receptacle removably secured to the lip adjacent the opening section, wherein the sealable stool receptacle is perforated across a section thereof for removal of the section.

\* \* \* \* \*